United States Patent
Yamamori et al.

(10) Patent No.: US 10,537,282 B2
(45) Date of Patent: Jan. 21, 2020

(54) MEDICAL IMAGE PROCESSING APPARATUS, MEDICAL IMAGE DIAGNOSIS APPARATUS AND RECORDING MEDIUM

(71) Applicant: Toshiba Medical Systems Corporation, Otawara-shi (JP)

(72) Inventors: Kyohei Yamamori, Otawara (JP); Tomohiro Kawasaki, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 79 days.

(21) Appl. No.: 15/484,526

(22) Filed: Apr. 11, 2017

(65) Prior Publication Data

US 2017/0290544 A1    Oct. 12, 2017

(30) Foreign Application Priority Data

Apr. 12, 2016    (JP) ................. 2016-079719

(51) Int. Cl.
*A61B 6/03* (2006.01)
*A61B 5/00* (2006.01)
*A61B 5/02* (2006.01)
*A61B 5/055* (2006.01)
*A61B 6/00* (2006.01)

(52) U.S. Cl.
CPC ........ *A61B 5/4848* (2013.01); *A61B 5/02007* (2013.01); *A61B 5/055* (2013.01); *A61B 5/7271* (2013.01); *A61B 6/032* (2013.01); *A61B 6/481* (2013.01); *A61B 6/504* (2013.01); *A61B 6/5217* (2013.01); *A61B 2576/026* (2013.01)

(58) Field of Classification Search
CPC ............ A61B 5/02007; A61B 5/02028; A61B 5/4848; A61B 5/489; A61B 6/03; A61B 6/032; A61B 6/504; A61B 6/5217
See application file for complete search history.

(56) References Cited

U.S. PATENT DOCUMENTS

| | | | |
|---|---|---|---|
| 9,087,147 B1 * | 7/2015 | Fonte | A61B 5/7275 |
| 9,192,347 B2 * | 11/2015 | Wakai | G06F 19/321 |
| 2005/0046644 A1 * | 3/2005 | Ohishi | A61B 6/481 345/643 |
| 2013/0259336 A1 * | 10/2013 | Wakai | G06F 19/321 382/130 |
| 2015/0032435 A1 | 1/2015 | Yagi et al. | |
| 2015/0164342 A1 * | 6/2015 | Choi | A61B 5/02007 600/407 |
| 2016/0306944 A1 * | 10/2016 | Grady | G06F 19/00 |
| 2016/0314601 A1 * | 10/2016 | Sankaran | G16H 50/50 |
| 2017/0347966 A1 * | 12/2017 | Yagi | A61B 5/02014 |

FOREIGN PATENT DOCUMENTS

| | | |
|---|---|---|
| JP | 2007-135894 | 6/2007 |
| JP | 2011-254861 | 12/2011 |
| JP | 5596866 | 9/2014 |

* cited by examiner

*Primary Examiner* — Eric D. Bertram
(74) *Attorney, Agent, or Firm* — Oblon, McClelland, Maier & Neustadt, L.L.P.

(57) ABSTRACT

According to the embodiments, a medical image diagnosis apparatus includes a memory and processing circuitry. The memory stores volume data on a target portion including a vessel network and a plurality of blood vessels connected to the vessel network. The processing circuitry extracts the vessel network and the blood vessels from the volume data. The processing circuitry analyzes how hemodynamics in the vessel network are after treatment of the vessels.

20 Claims, 9 Drawing Sheets

Example of embolization order 1→2→3

| Embolization order | Artery to be embolized | CFD parameters | | | | Recommendation |
|---|---|---|---|---|---|---|
| | | Target 1 | Target 2 | Target 3 | Target 4 | |
| 1→2→3 | 1 | ×× | ○○ | △△ | △△ | 1 |
| | 2 | △△ | ○○ | △△ | □□ | |
| | 3 | △△ | ×× | ○○ | ▽▽ | |
| 1→3→2 | 1 | ×× | ○○ | △△ | △△ | 2 |
| | 3 | ×× | ○○ | ×× | □□ | |
| | 2 | ○○ | △△ | △△ | □□ | |
| 2→1→3 | 2 | ×× | ○○ | △△ | △△ | 3 |
| | 1 | △△ | ×× | ○○ | ▽▽ | |
| | 3 | ×× | ○○ | △△ | □□ | |
| 2→3→1 | 2 | ×× | ○○ | △△ | △△ | NG |
| | 3 | ×× | ○○ | △△ | □□ | |
| | 1 | △△ | ×× | ○○ | ▽▽ | |
| 3→1→2 | 3 | ×× | ○○ | △△ | □□ | NG |
| | 1 | ○○ | △△ | ×× | △△ | |
| | 2 | △△ | ×× | △△ | ×× | |
| 3→2→1 | 3 | ×× | ○○ | △△ | □□ | NG |
| | 2 | ×× | △△ | ○○ | ×× | |
| | 1 | ×× | ○○ | △△ | □□ | |

| Embolization order | Target blood vessel | CFD parameters | | Recommendation |
|---|---|---|---|---|
| | | Average | Deviation | |
| 1→2→3 | 1 | | | 2 |
| | 2 | | | |
| | 3 | | | |
| | 4 | | | |
| 1→3→2 | 1 | | | 1 |
| | 2 | | | |
| | 3 | | | |
| | 4 | | | |
| 2→1→3 | 1 | | | 3 |
| | 2 | | | |
| | 3 | | | |
| | 4 | | | |
| 2→3→1 | 1 | | | NG |
| | 2 | | | |
| | 3 | | | |
| | 4 | | | |
| 3→1→2 | 1 | | | NG |
| | 2 | | | |
| | 3 | | | |
| | 4 | | | |
| 3→2→1 | 1 | | | NG |
| | 2 | | | |
| | 3 | | | |
| | 4 | | | |

FIG. 7

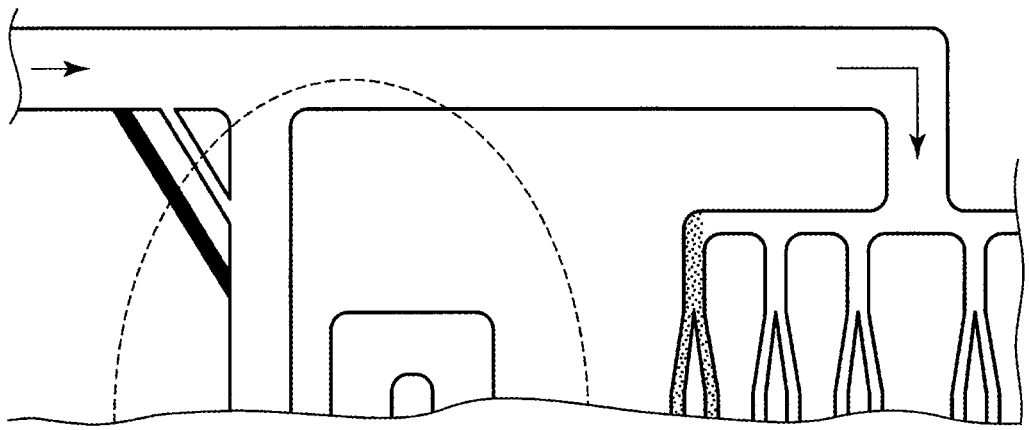
FIG. 9A
Flow rate of blood
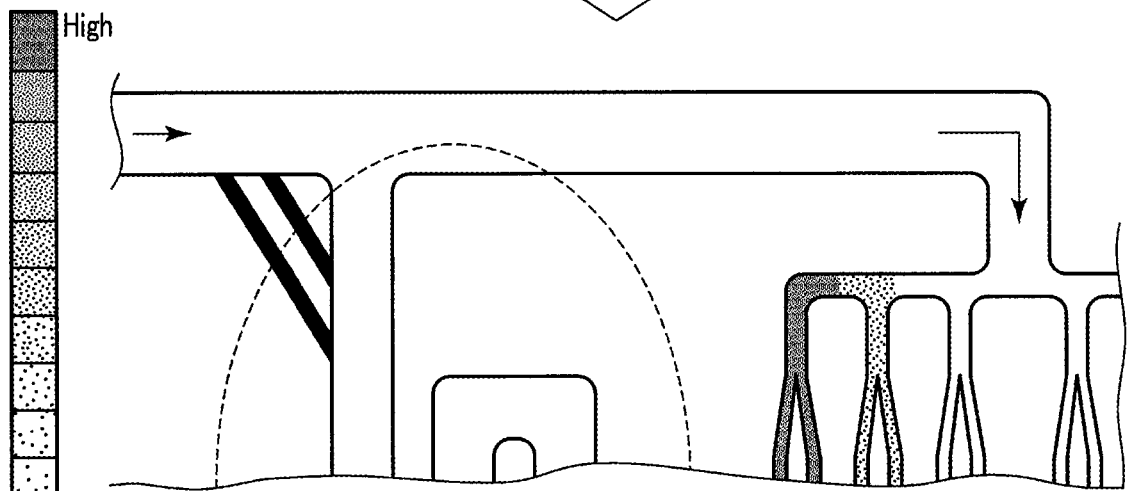
FIG. 9B
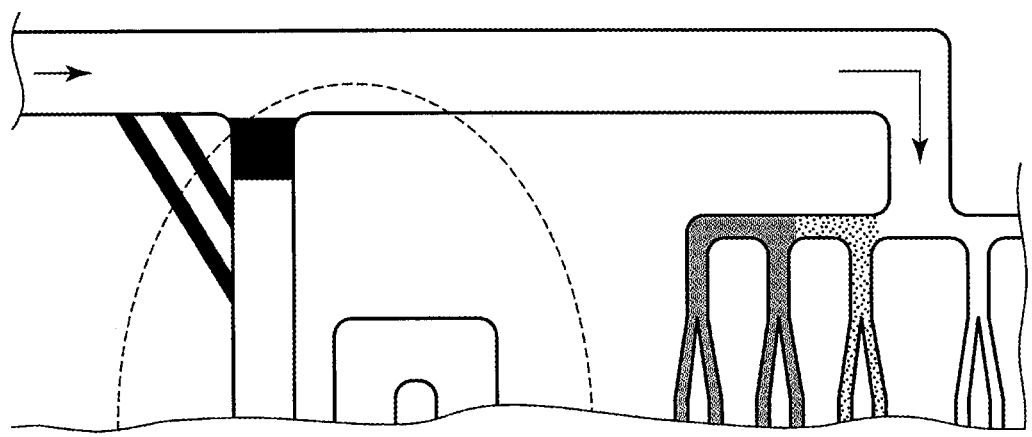
FIG. 9C  Example of embolization order 1→2→3

MEDICAL IMAGE PROCESSING APPARATUS, MEDICAL IMAGE DIAGNOSIS APPARATUS AND RECORDING MEDIUM

CROSS-REFERENCE TO RELATED APPLICATIONS

This application is based upon and claims the benefit of priority from Japanese Patent Application No. 2016-079719, filed Apr. 12, 2016, the entire contents of which are incorporated herein by reference.

Field

Embodiments described herein relate generally to a medical image processing apparatus, a medical image diagnosis apparatus, and a recording medium.

Background

Where the blood vessels in the brain are normal, blood flows from an artery to a veil by way of capillaries. In some rare cases, however, the artery short-circuits the capillaries and is connected directly to the veil, which is a congenital disease referred to as anteriovenous malformation.

The blood vessel mass between feeders and drainers is referred to as a nidus. In the neighborhood of the nidus, the vein having a thin vessel wall is expanded due to an increase in the blood flow. Since this increases the possibility of the bleeding in the brain, treatment may be required basically.

The treatment includes a surgical treatment, a radiation treatment, an endovascular treatment (embolization), etc. Which treatment should be used is determined based on the size and position of the nidus.

The endovascular treatment, feeders are embolized one by one either physically or by use of a chemical agent. Where the number of feeders to be embolized is large, the treatment has to be performed a number of times. If many blood vessels are embolized in one treatment, the embolization significantly changes the hemodynamics, and a large quantity of blood collected in a particular location may damage the downstream blood vessels (including capillaries), increasing the possibility of bleeding. If the blood flow in veins decreases, the risk of the embolization increases. A surgeon has to determine a plan of treatment in a comprehensive manner in due consideration of these risks.

As it stands now, each time one blood vessel is embolized, the surgeon carefully observes the state of the patient and determines whether or not to continue the operation. This means that the operation is performed in an impromptu manner, and it cannot be denied that an unexpected incident will occur. Where there are a number of blood vessels to be embolized, no method is available to know in which order they should be embolized to reduce risk. Under the circumstances, there is a demand for a technique that enables accurate risk evaluation prior to an actual operation.

BRIEF DESCRIPTION OF THE DRAWINGS

FIG. 7 shows an example of how indexes related to CFD parameters at analysis target points p1 to p4 are with respect to each of the embolization orders.

FIG. 9A illustrates a state where feeder a1 is embolized.

FIG. 9B illustrates a state where feeders a1 and a2 are embolized.

FIG. 9C illustrates a state where all feeders a1-a3 are embolized.

DETAILED DESCRIPTION

In general, according to the embodiments, a medical image diagnosis apparatus includes a memory and processing circuitry. The memory stores volume data on a target portion including a vessel network and a plurality of blood vessels connected to the vessel network. The processing circuitry extracts the vessel network and the blood vessels from the volume data. The processing circuitry analyzes how hemodynamics in the vessel network are after treatment of the vessels.

Figure 1:
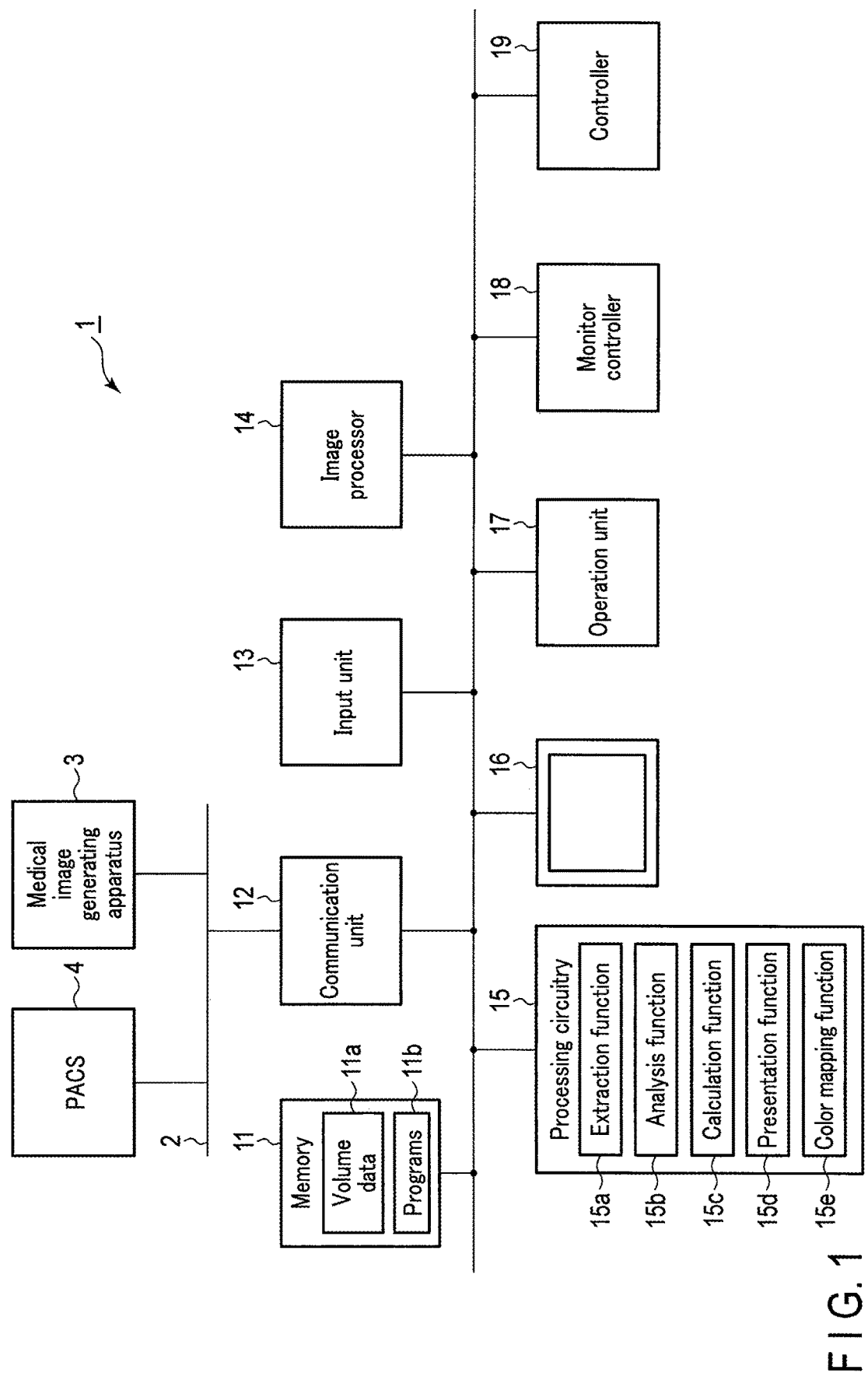
FIG. 1 is a functional block diagram showing an example of a medical image processing apparatus according an embodiment.

FIG. 1 is a functional block diagram showing an example of a medical image processing apparatus according an embodiment. The medical image processing apparatus 1 comprises a memory 11, a communication unit 12, an input unit 13, an image processor 14, processing circuitry 15, a monitor 16, an operation unit 17, a monitor controller 18 and a controller 19.

The memory 11 is, for example, a semiconductor memory, such as a random access memory (RAM), a read-only memory (ROM), a flash memory, or a synchronous dynamic RAM (SDRAM), or a nonvolatile memory such as an erasable programmable ROM (EPROM) or an electrically erasable programmable ROM (EEPROM).

The memory stores volume data 11a and programs 11b. The volume data 11a is data on three-dimensional images of, for example, brain areas of a subject. The three-dimensional images are acquired by modalities, including an X-ray computed tomography apparatus, a magnetic resonance imaging apparatus, an X-ray diagnose apparatus and an ultrasonic diagnosis apparatus.

The communication unit 12 communicates with an in-hospital local area network (LAN) 2 or an external communication network (such as the Internet or a cloud computing system) and exchanges various kinds of data.

The input unit 13 acquires volume data on an image processing target from a medical image generating apparatus 3 or from a picture archiving and communication system (PACS) by means of the communication unit 12. The medical image generating apparatus 3 is, for example, an X-ray computed tomography apparatus (CT apparatus) or a magnetic resonance imaging apparatus (MRI apparatus). The volume data can be acquired using XR technique (3D reconstruction imaging).

In the description given below, reference will be made to the case where the input unit 13 acquires data on a three-dimensional image of the head of a subject, which is a target portion imaged by the CT apparatus. For example, the CT apparatus dynamically scans the brain of the subject using X-rays after a contrast medium is injected into the brain, and collects data on three-dimensional images of a plurality of time phases.

The image processor 14 performs three-dimensional image processing, such as multi planar reconstruction (MPR) and volume rendering, and generates a three-dimensional blood vessel model image from the volume data 11a. In embodiments, it is assumed that the blood vessel model image includes a nidus, a feeder connected to the nidus, and a branching vessel.

In embodiments, the blood vessels which are located downstream of the position where an artery is connected to a nidus and which are connected to capillaries will be referred to as branching vessels. Each of the branching vessels further branches as capillaries. In other words, the branching vessels may include capillaries. In embodiments, the structure including the nidus and the capillaries will be referred to as a vascular network. A target portion includes this vascular network.

The processing circuitry 15 includes, for example, a processor and a memory. The processing circuitry 15 has the function of an information processing apparatus (computer) and controls the medical image processing apparatus 1. The processing circuitry 15 reads various programs 11b related to control processing from the memory 11. After reading the programs 11b, the processing circuitry 15 has an extraction function 15a, an analysis function 15b, a calculation function 15c, a presentation function 15d and a color mapping function 15e. In other words, the processing circuitry 15 reads, from the memory 11, programs related to the extraction function 15a, the analysis function 15b, the calculation function 15c, the presentation function 15d and the color mapping function 15e.

The processing circuitry 15 loads the program related to the extraction function in its memory, and executes the program to realize the extraction function 15a. At the time, the processing circuitry 15 functions as an extraction unit. The extraction function 15a analyzes the volume data 11a by use of existing image processing technology and extracts a nidus connected to an artery, feeders for feeding blood to the nidus, and branching vessels which are located downstream of the position where the artery is connected to the nidus and which branch from the artery. In short, the extraction function 15a extracts the nidus, the feeders and the branching vessels.

Although the nidus and the feeders were mentioned as an example of a malformed area having an anomalous vascular structure, these are not restrictive. Any blood vessel shape and any blood vessel disease may be extracted provided that they may be risky to the human body.

A nidus, feeders and branching vessels may be automatically extracted by image analysis. This automatic extraction may be combined with user's manual input, which is auxiliary input. For example, after a vascular structure is extracted from the volume data, the extracted vascular structure is displayed on the monitor 16. From the vascular structure, the user designates an area corresponding to the nidus and areas corresponding to the artery and vein by operating the input unit 13. Based on the designated nidus, artery and vein, blood vessels connected to them are specified. By so doing, the processing circuitry 15 (extraction unit) can specify the blood vessels as feeders and branching vessels.

The processing circuitry 15 loads the program related to the analysis function in its memory, and executes the program to realize the analysis function 15b. At the time, the processing circuitry 15 functions as an analysis unit. The analysis function 15b performs simulation analysis using computational fluid dynamics (CFD), for each of the cases where feeders are embolized in different orders (hereinafter referred to as embolization orders). In other words, the analysis function 15b performs CFD analysis for each embolization order, calculates a CFD parameter serving as a fluid parameter, and simulates hemodynamics for each embolization order.

For example, if there are three feeders and each feeder has one portion that can be embolized, six embolization orders are available (permutation operation: 3×2×1). If there is one feeder and this feeder has three portions that can be embolized, six embolization orders are available (permutation-combination operation: 3×2×1). That is, there are three portions which are to be embolized first, there are two portions which are to be embolized next, and there is one portion which is to be embolized finally.

If there are three feeders and each of these feeders has two portions that can be embolized, the embolization orders available are 720 (=6!). As can be seen from this, the embolization orders that can be presented change in accordance with the number of embolizable portions included in a simulated target region.

As described above, where there are many portions that can be embolized, embolization orders are very large in number, and hemodynamics for all these orders cannot be simulated. In such a case, simulation is not performed for all orders. Instead, an embolization portion whose risk index value exceeds a threshold when it is embolized first may be detected, and the permutation of the case where that embolization portion is embolized first may be removed from the simulation. By decreasing the number of embolization orders which are to be simulated, simulation results can be obtained at high speed.

CFD parameters are, for example, a flow rate of blood, a blood pressure, and a wall shear stress (WSS). The CFD parameters can be calculated, for example, for each of analysis target points determined on an extracted branching vessel.

In particular, the analysis function 15b calculates hemodynamics for each of the cases where a plurality of feeders are embolized in different orders and at different portions. As can be seen from this, not only the embolization orders but also embolization positions may be added as indexes when operation risks are evaluated.

The processing circuitry 15 loads the program related to the calculation function in its memory, and executes the program to realize the calculation function 15c. At the time, the processing circuitry 15 functions as a calculation unit. The calculation function 15c calculates a risk for each of the embolization orders (which may be referred to as operation cases), based on the results of the CFD analysis. For example, the calculation function 15c calculates a risk based on how stable the CFD parameters are before and after the operation. The risk may be evaluated based on results of comparison between the CFD parameters and predetermined thresholds.

The processing circuitry 15 loads the program related to the presentation function in its memory, and executes the program to realize the presentation function 15d. At the time, the processing circuitry 15 functions as a presentation unit. The presentation function 15d presents operation cases in the risk ascending order, based on the calculated risks. Only one recommendable operation case, namely, the operation case whose risk is lowest, may be presented.

The processing circuit 15 loads the program related to the color mapping function in its memory, and executes the program to realize the color mapping function 15e. At the time, the processing circuitry 15 functions as a color mapping unit. The color mapping function 15e maps the calculated CFD parameters in different colors on the branching vessels in a three-dimensional model image generated by image processing. To be more specific, the color mapping function 15e generates an image (hereinafter referred to as a map image) in which the colors corresponding to the values of the CFD parameters are allocated to the pixels of a three-dimensional model image generated by the image processor 14. The generated map image is displayed on the monitor 16.

The monitor 16 is a human-machine interface configured to display various medical images and text information. As the monitor 16, a CRT display, a liquid crystal display, an organic EL display, a plasma display or the like can be used.

The operation unit 17 accepts various instructions and information inputs from a user. As the operation unit 17, a pointing device (such as a mouse or a trackball), a selection device (such as a mode change switch), an input device (such as a keyboard) or the like may be employed, as needed.

The monitor controller 18 displays, on the monitor 16, a blood vessel model image on which a map image is superimposed, a volume rendering image, or the like.

The controller 19 functions as a core element of the medical image processing apparatus 1. Upon receipt of a request for starting the risk evaluation processing from the operation unit 17, the controller 19 controls the portions of the medical image processing apparatus 1 to execute the risk evaluation processing.

The medical image processing apparatus 1 may employ a general-purpose computer apparatus as a basic hardware element. The medical image processing apparatus 1 can perform quantitative evaluation processing on an operation risk by causing the processor (CPU: central processing unit) of the computer apparatus to execute an image processing program. The image processing program is pre-installed in the computer apparatus. The image processing program may be distributed to the computer apparatus in the form of a removable recording medium such as a magnetic disk, a magnetooptical disk, an optical disk, or a semiconductor memory, or by way of a network. The distributed image processing program is installed in the computer apparatus and executed at a proper time.

Part or all of the above-mentioned portions may be realized as hardware elements. Alternatively, each of the above-mentioned portions may be a combination of a hardware element and software control. Next, a plurality of embodiments will be described based on the above configuration.

<First Embodiment>

Figure 2:
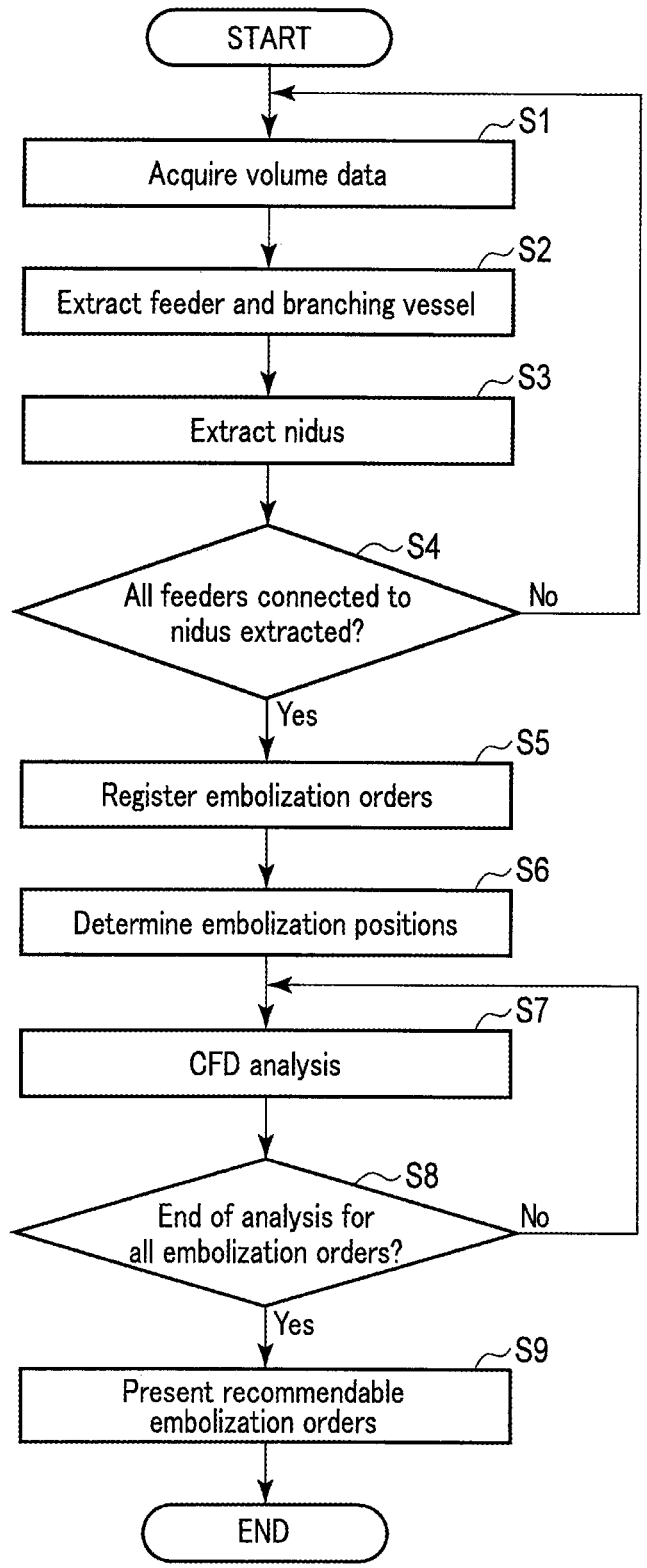
FIG. 2 is a flowchart showing an example of procedures performed by the medical image processing apparatus 1 shown in FIG. 1.

FIG. 2 is a flowchart showing an example of a procedure performed by the medical image processing apparatus 1 shown in FIG. 1. Referring to FIG. 2, the medical image processing apparatus 1 acquires volume data 11a from the CT apparatus, the MR apparatus or the XR imaging apparatus (step S1). Next, the medical image processing apparatus 1 performs image processing with respect to the acquired volume data 11a and extracts a vascular structure. By the image processing, the medical image processing apparatus also extracts a nidus in a blood vessel, a feeder and a branching vessel (steps S2 and S3). Steps S1 to S3 are repeated until all feeders connected to the nidus are extracted (step S4).

Figure 3:
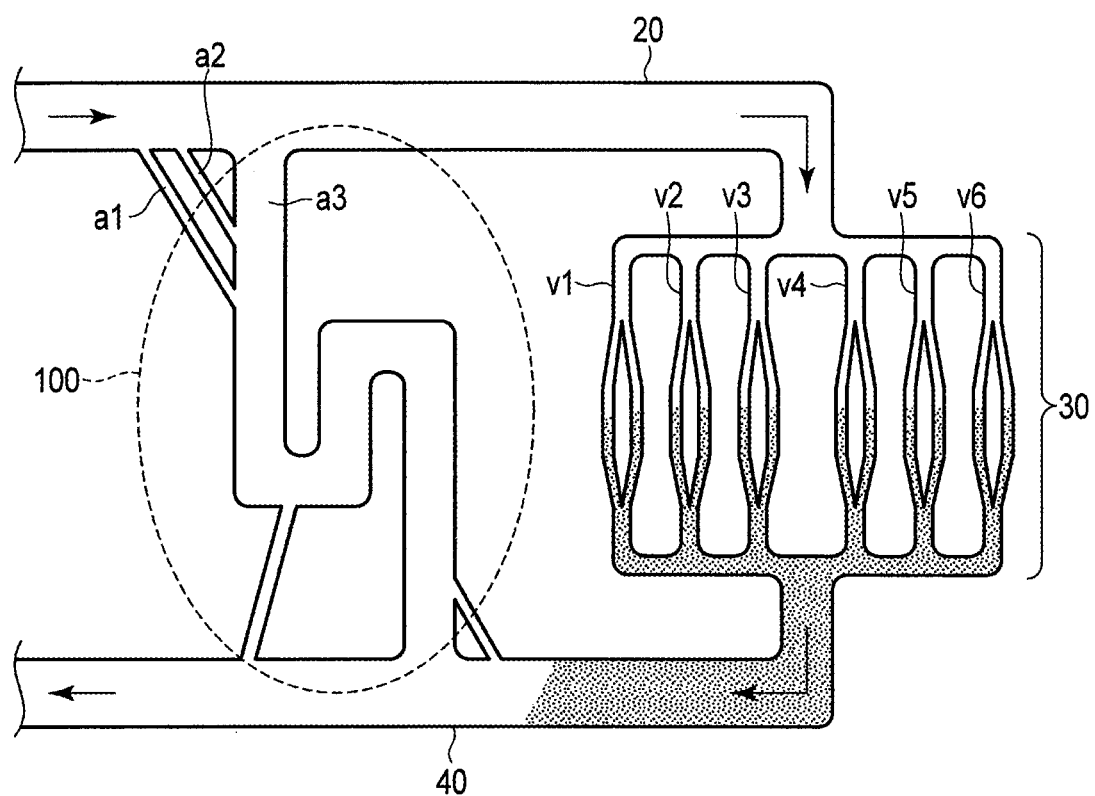
FIG. 3 schematically illustrates an example of anteriovenous malformation.

FIG. 3 schematically illustrates an example of anteriovenous malformation. In FIG. 3, the region within the broken-line circle is a nidus 100. The nidus 100 is connected to the artery 20 by way of feeders a1 to a3. The artery branches into a plurality of blood vessels (branching vessels v1 to v6) at a position located downstream of the position where the artery 20 is connected to the nidus 100. Each branching vessel further branches into thin blood vessels, which in turn are connected to capillaries 30. The capillaries 30 extend deep in the brain and then join together, forming a vein 40. Since the nidus 100 is connected to the vein 40 as well, it bypasses the capillaries 30.

Let us assume that the nidus 100, feeders a1 to a3 and branching vessels v1 to v6 shown in FIG. 3 are extracted in steps S2 and S3 shown in FIG. 2. Input volume data 11a does not require a high spatial resolution. If the spatial resolution of the input volume data 11a enables analysis of the blood vessel shape, such a spatial resolution is sufficient. Provided such a spatial resolution, the volume data 11a is not limited to that obtained by the CT apparatus, MR apparatus or XR imaging apparatus (3D reconstruction imaging apparatus).

Referring to the flowchart shown in FIG. 2, the orders in which the feeders are embolized (embolization orders) are registered in the medical image processing apparatus 1 (step S5). For example, all embolization orders can be registered. With respect to the three feeders a1 to a3 shown in FIG. 3, the following six embolization orders can be registered: a1→a2→a3, a1→a3→a2, a2→a1→a3, a2→a3→a1, a3→a1→a2, and a3→a2→a1.

Part of the embolization orders may be registered. To narrow down the embolization orders, anatomical information such as the position and thickness of a blood vessel may be used. For example, only embolization orders in which a thin blood vessel is embolized first may be registered; conversely, only embolization orders in which a thick blood vessel is embolized first may be registered. Furthermore, after all embolization orders are registered, the user may select some of them for use in the subsequent analysis. For example, only two embolization orders, a1→a2→a3 and a1→a3→a2, may be registered based on the user's selection.

Figure 4:
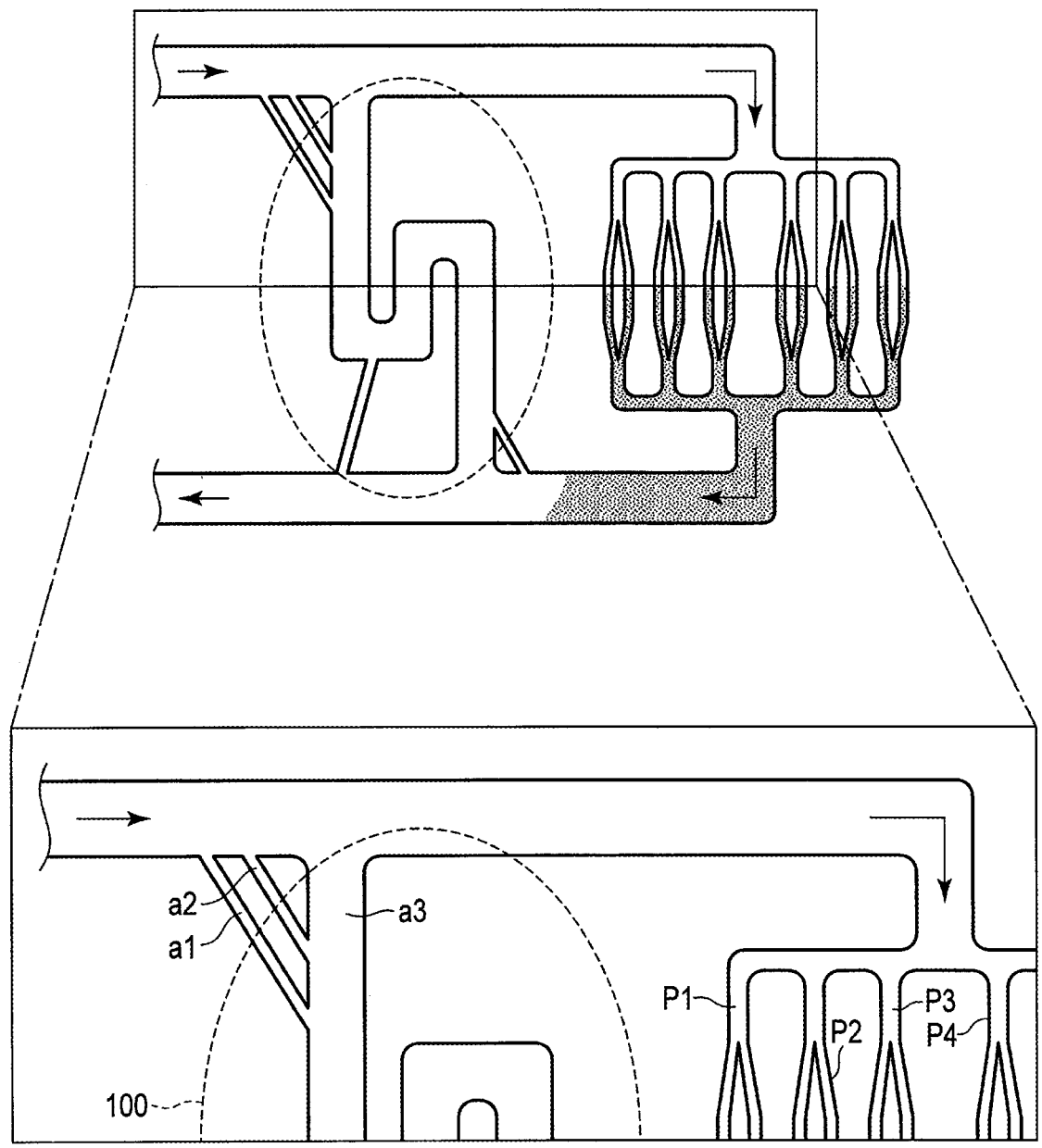
FIG. 4 shows an example of an analysis target point of hemodynamics.

In step S5, a point (analysis target point) at which hemodynamics are analyzed is set by the user's manual operation. For example, as shown in FIG. 4, a plurality of analysis target points (p1 to p4) can be set on the upstream side of the portions between branching vessels and capillaries.

Figures 5, 6:
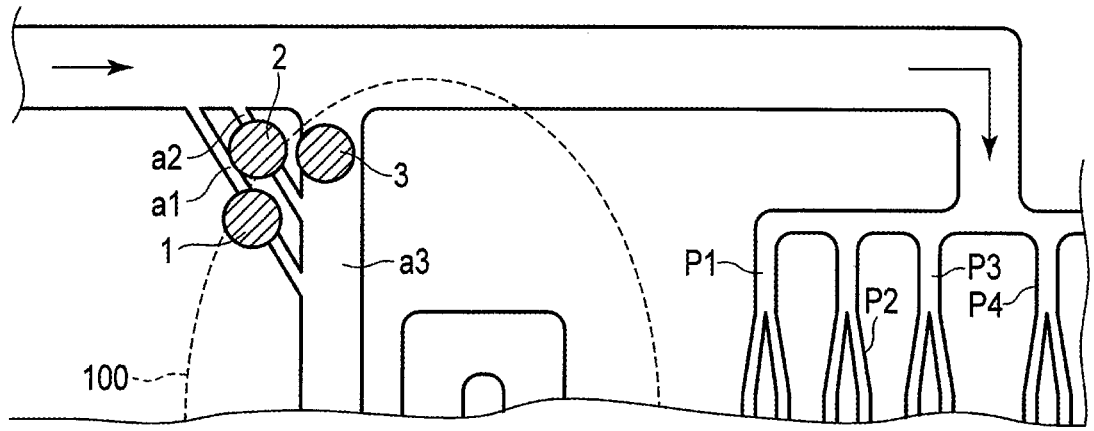
FIG. 5 shows an example of embolization points 1 to 3.
FIG. 6 shows an example of results of CFD analysis performed for each embolization order.

Subsequently, embolization positions are determined for feeders a1 to a3 (step S6). It should be noted that the optimal positions of embolization positions 1 to 3 shown in FIG. 5 are not limited to the root portions of the nidus, namely, positions close to the nidus. There may be a case where a favorable prognosis can be expected by shifting the embolization positions to a deeper side, namely, to positions away from the nidus. The embolization positions 1 to 3 may be manually determined by the user.

Optimal embolization positions can be determined by CFD analysis. Specifically, the medical image processing apparatus 1 (the program) sets embolization points on blood vessels (or arranges embolization regions of constant size), performs CFD analysis, and automatically detects embolization positions where the blood streams stop, based on the results of the CFD analysis.

Next, the medical image processing apparatus 1 executes CFD analysis (step S7). That is, the analysis function 15b calculates fluid parameters at the analysis target points p1 to p4 by CFD simulation, for each of the embolization orders registered in step S5.

FIG. 6 shows an example of results of the CFD analysis performed for each embolization order. In FIG. 6, symbols ○, Δ, □ and × indicate values. It should be noted that the same symbols do not necessarily mean that the values indicated by them are the same.

Embolization order 1→2→3 means that feeders are embolized in the order of a1→a2→a3, and targets 1 to 4 correspond to analysis target points p1 to p4. When the CFD analysis is completed with respect to all registered embolization orders, the medical image processing apparatus 1 evaluates how the CFD parameters at the analysis target points p1 to p4 change with respect to the respective embolization orders.

FIG. 7 shows an example of how indexes related to CFD parameters at the analysis target points p1 to p4 are in each of the embolization orders. The indexes related to the CFD parameters are, for example, average values or standard deviations of the CFD parameters obtained when the embolization is performed in order. The calculation function 15c calculates average values and standard deviations of the CFD parameters with respect to each of the embolization orders and evaluates the risk of each embolization order, based on the stability of the CFD parameters.

Figure 8:
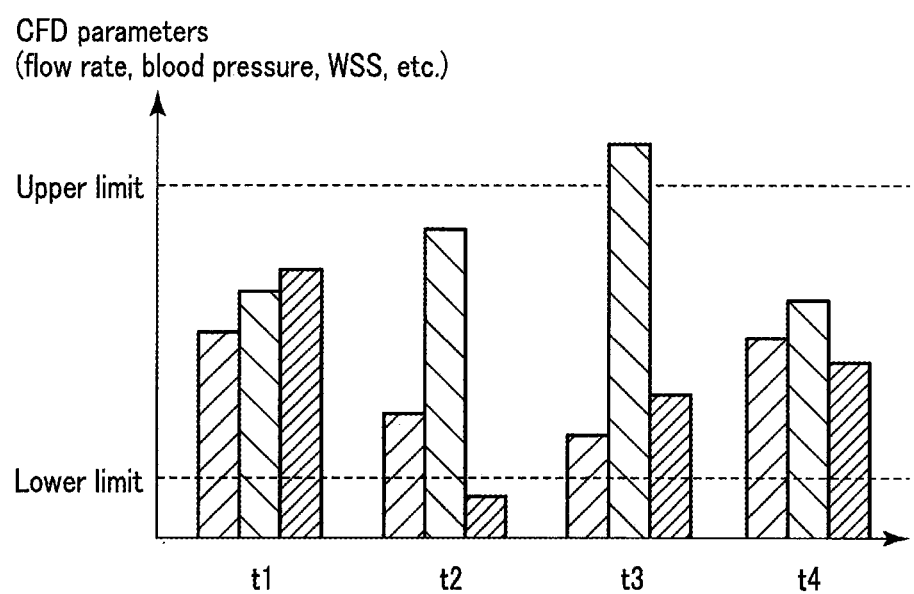
FIG. 8 illustrates an example of a risk evaluation technique.

FIG. 8 illustrates an example of a risk evaluation technique. The histogram in FIG. 8 shows how simulation values of the CFD parameters are when feeders a1 to a3 are embolized in a given embolization order, and the simulation values are indicated for each of analysis target points p1 to p4. Referring to FIG. 8, the CFD parameters at analysis target points p1 and p4 are comparatively stable, but the CFD parameters at analysis target points p2 and p3 varies greatly, deviating from the upper or lower limit. The calculation function 15c determines that the embolization orders resulting in such unstable CFD parameters are at high risk and excludes such embolization orders from the recommended orders.

When the analysis for all embolization orders ends and the risk evaluation is completed (Yes in step S8), the calculation function 15c specifies which embolization order results in the most stable CFD parameters, and supplies the result to the presentation function 15e. Being stable indicates that the CFD parameters do not much vary at times when the points are embolized. The state when a certain CFD parameter at such embolization times is less than the lower limit or exceeds the upper limit may be evaluated as not being stable (being unstable). The presentation function visually presents at least one recommendable embolization order on the monitor 16, based on the risks (the degrees of stability) (step S9).

FIGS. 9A, 9B and 9C are schematic diagrams illustrating relationships between the embolization of feeders and the blood flow rates. FIG. 9A illustrates a state where feeder a1 is embolized. FIG. 9B illustrates a state where feeders a1 and a2 are embolized. FIG. 9C illustrates a state where all feeders a1-a3 are embolized.

Since the blood flow rate changes in accordance with an increase in the number of points embolized, a CFD parameter reflecting the blood flow rate varies. The color mapping function 15e of the processing circuitry 15 generates a map image in which the color corresponding to the value of a CFD parameter or the color corresponding to the variation of the CFD parameter is assigned to each of the pixels of a three-dimensional model image of blood vessels. In FIGS. 9A, 9B and 9C, how the hemodynamics in each branching vessel vary is indicated by the hatchings. The difference in hatchings is a difference in color. A blood vessel in which the CFD parameter exceeds a threshold may be displayed in a different color.

If the CFD parameter exceeds the threshold at the end of the embolization of all points, the blood vessel showing such a CFD parameter may be displayed in a different color. Alternatively, if the CFD parameter exceeds the threshold before all points are embolized, the blood vessel showing such a CFD parameter may be displayed in a different color.

As described above, according to the present embodiment, a three-dimensional blood vessel model is extracted based on volume data obtained by CT or MRI, and a nidus, feeders and branching vessels are extracted. In addition, simulation analysis using CFD is carried out based on the three-dimensional blood vessel model, for each of the cases where the feeders are embolized in different permutations and combinations. Based on the results of the simulation analysis, how the CFD parameter varies at a designated analysis point is evaluated.

The embolization order that ensures the most stable state of a CFD parameter is a recommendable order. An embolization order that undergoes a great change in CFD parameter each time embolization is performed is an order having low priority. In particular, if an embolization order causes the CFD parameter to exceed or become lower than a threshold, such an embolization order should not be adopted.

For example, an embolization order that results in the smallest standard deviation of a CFD parameter may be recommended. An embolization order to be recommended may be determined based on the comparison between the value of a CFD parameter and a predetermined threshold. For example, a CFD parameter may be expressed in the form of a graph, and embolization orders which are within the range determined by the upper and lower limits may be indicated as embolization order candidates to be applied to an actual operation. The upper and lower limits may be determined by the user; alternatively, generally recommended values may be used.

As can be seen from the above, the operator can know, prior to an actual operation, how the hemodynamics change when the respective feeders are embolized. Thanks to this, an operation risk, such as bleeding caused by a rapid change in hemodynamics, can be lowered. How the blood flow rate changes when the respective feeders are embolized can be predicted, and recommended embolization orders can be confirmed. This information is helpful to a surgeon when the surgeon develops a plan for an endovascular treatment. According to the first embodiment, the risk related to changes in hemodynamics can be quantitatively evaluated, and this helps the surgeon develop a treatment plan.

<Second Embodiment>

A surgical procedure which guides a catheter to a position near an embolization position and injects an embolic agent to embolize a blood vessel, is known in the art. An embodiment applicable to this surgical procedure will be described.

A liquid embolic agent is known in which a high-molecular compound (e.g., ethylene vinyl alcohol copolymer) is dissolved in an organic solvent (DMSO). When this embolic agent is injected in a blood vessel, the DMSO is diffused and the high-molecular compound is precipitated. The precipitated high-molecular compound embolizes the blood vessel.

If the injection of the embolic agent is not performed properly (for example, the selection of an improper embolic agent, an improper injection position, an improper injection amount, etc.), there may be a case where the embolic agent flows back into other feeders, a case where the embolic agent flows back toward the catheter and the catheter cannot be pulled off, a case where the embolic agent flows back into a normal-state blood vessel, or the like. Each of these cases is dangerous to the patient.

In the second embodiment, therefore, the behavior of the injected embolic agent is simulated by fluid analysis. That is, where the injected embolic agent flows is calculated by fluid analysis.

In the second embodiment, the analysis function 15b shown in FIG. 1 simulates, by fluid analysis, how a designated embolic agent flows from an injection position when that embolic agent is injected in a designated amount.

For example, the kind of embolic agent, an injection amount and an injection position (which can be regarded, in effect, as the distal end of a catheter) are designated as analysis parameters for fluid analysis. An embolization position may also be designated as an analysis parameter. The kind of embolic agent is registered in a database in association with the viscosity. If the kind of embolic agent is changed, the viscosity data is changed, and fluid analysis is performed again.

When simulation is performed, the user determines at least which region of a blood vessel should be embolized, and determines an injection position. If the results of simulation show that an embolic agent flows upstream from the injection position or that the embolic agent flows into a blood vessel designated as a feeder, then the analysis parameters corresponding to this situation are registered as "NG."

If the simulation results indicate "NG," the position and injection amount designated by the user are changed slightly, and the fluid analysis is performed again. The fluid analysis is repeated until an desirable injection position and injection amount are found, which do not cause the embolic agent to flow backward or into an artery and which enable the predetermined embolization region to be reliably embolized.

Figure 10:
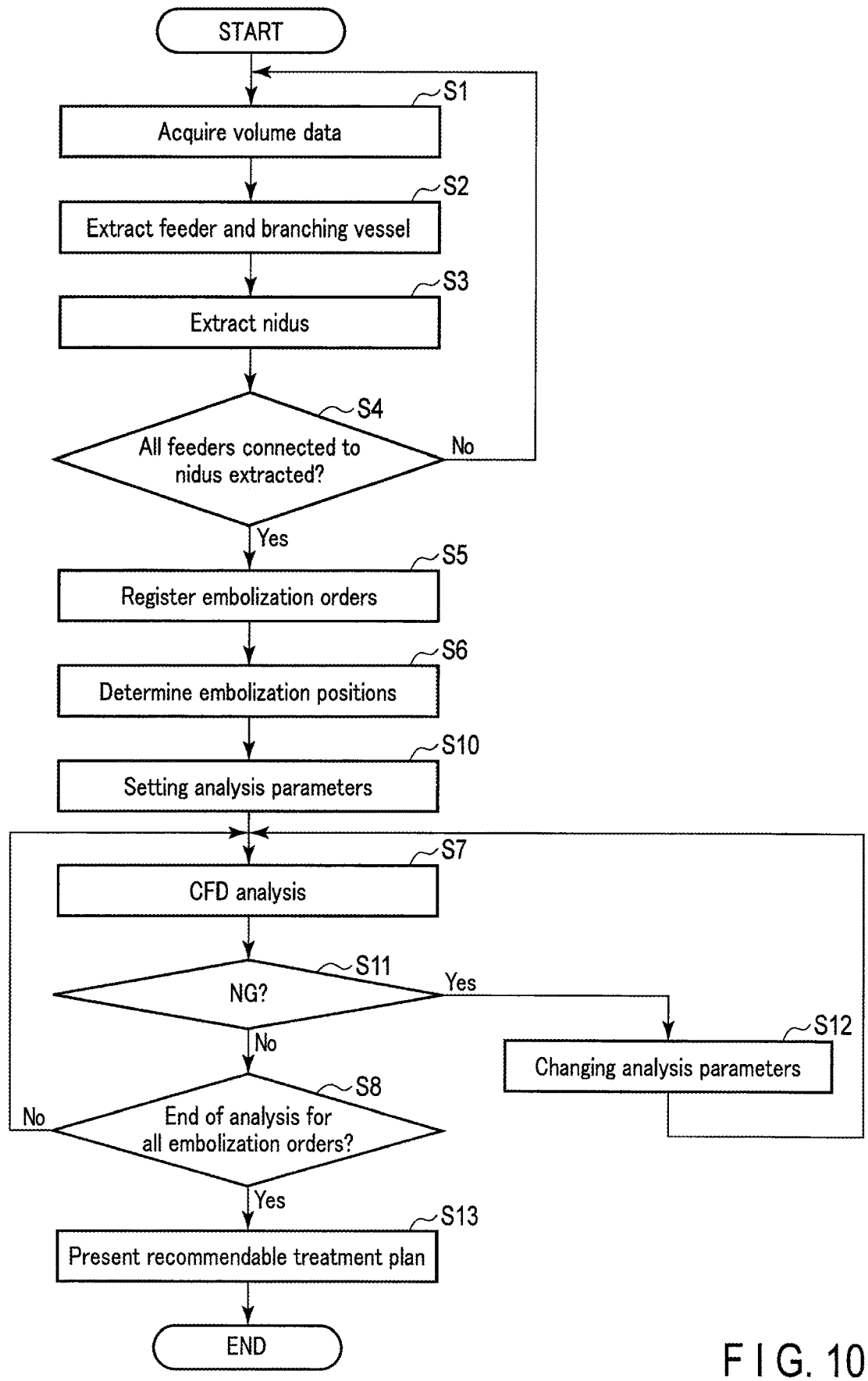
FIG. 10 is a flowchart showing an example of procedures performed by a medical image processing apparatus 1 according the second embodiment.

FIG. 10 is a flowchart showing an example of procedures performed by a medical image processing apparatus 1 according the second embodiment. Of the steps shown in FIG. 10, those which are similar to the steps shown in FIG. 2 will not be described.

When embolization positions are determined in step S6 in FIG. 10, the medical image processing apparatus 1 accepts analysis parameters (step S10). The analysis parameters are designated by the user, using the operation unit 17. The designated analysis parameters are stored in the memory 11.

Next, the medical image processing apparatus 1 executes CFD analysis based on the designated analysis parameters (step S7). To be specific, the analysis function 15b simulates, by fluid analysis, how the designated embolic agent flows from the injection position when the embolic agent is injected in a designated amount. If the results of simulation indicate "NG" (Yes in Step S11), different values are set as the analysis parameters (step S12), and CFD analysis is executed again.

When the analysis for all embolization orders ends and the risk evaluation is completed (Yes in step S8), the analysis function 15b specifies which treatment plan is recommendable. The specified treatment plan is supplied to the presentation function 15e. The presentation function 15e visually presents at least one treatment plan on the monitor 16, together with the combination of related analysis parameters (step S13).

In this manner, the fluid analysis is repeatedly executed, with the analysis parameters being adjusted finely. The simulation may be ended if "NG" is no longer indicated. If "NG" continues to be indicated, the user may be informed of this and prompted to replace the embolic agent with another. In addition, the injection position the injection amount of the embolic agent may be automatically adjusted in such a manner that the NG is not indicated.

As described above, according to the second embodiment, a list of treatment plans, including recommendable embolization orders and embolization positions, is displayed. At least one recommendable embolization order (treatment plan) may be displayed on the monitor 16, as in the first embodiment. Alternatively, a number of treatment plans may be presented as a list in the risk ascending order.

Preferably, a treatment plan including procedures indicated as NG is not displayed on the monitor 16. Alternatively, such a treatment plan may be displayed with a warning.

According to the second embodiment, the risk related to changes in the hemodynamics can be quantatively evaluated, and this helps the doctor develop a treatment plan.

The embodiments described above are not restrictive. For example, when the embolization orders are narrowed down, such indexes as the position and thickness of a blood vessel may be added as information for making a decision. Where the number of niduses is not less than a threshold (e.g., 6), embolization orders may be determined, with the blood vessels being limited to those having more than a predetermined thickness.

Conversely, there may be a case where only two of three feeders are embolized. Such a case may be taken into account when evaluating the risk or determining a recommendable order. This is because part of the blood vessels may be left untreated in an actual operation. When making a surgical plan in such a case, the user designates which embolization points should be excluded from among the embolization points extracted.

It should be noted that a CFD analysis does not have to be made for all permutations and combinations of a plurality of feeders and a plurality of embolization points. The CFD analysis may be made only for some of the cases extracted as candidates, and embolization orders having low risk may be selected and recommended. The candidates may be selected by the operator; alternatively, they may be extracted based on the calculation performed by the apparatus.

The procedure for stopping the blood stream in a feeder is not limited to the embolization described above. For example, in a craniotomy, the blood stream in blood vessels may be stopped by clipping (the blood vessels are pinched in order with clips), or blood vessels may be removed by use of a surgical knife. A radiation treatment may be applied to reduce the size of a nidus or a phyma. The configuration described above is applicable to any of these procedures.

The programs for realizing the medical image processing apparatus 1 may be recorded in a computer-readable recording medium. In this case, a computer system reads the programs recorded in the recording medium and executes them to realize the image processing. The term "computer system" used herein may include an operating system (OS) or hardware such as a peripheral device.

The computer-readable recording medium is a recordable nonvolatile memory (such as a flexible disk, a magnetooptical disk, a ROM or a flash memory), a portable medium (such as a CD-ROM), or a hard disk built in in a computer system.

Furthermore, a computer-readable recording medium may be any type of storage capable of storing programs for a certain length of time, including a server to which programs are transmitted by way of a network (such as the Internet) or a communication line (such as a telephone line), and a volatile memory of a computer system serving as a client (such as a dynamic random access memory (DRAM)).

The programs may be transmitted from the computer system incorporating a storage in which they are stored to another computer system, by way of a transmission medium or by use of a carrier wave for the transmission medium. The "transition medium" used herein is intended to refer to a medium capable of transmitting information, including a network (communication network) such as the Internet or a communication line such as a telephone line.

The term "processor" used in the above description indicates, for example, a central processing unit (CPU), a graphics processing unit (GPU), or circuits such as an application specific integrated circuit (ASIC), a programmable logic device (for example, a simple programmable logic device (SPLD), a complex programmable logic device (CPLD), or a field programmable gate array (FPGA)).

The processor reads the programs stored in the storage circuit and executes them to realize the respective functions. The programs may be incorporated in the circuit of the processor, instead of storing them in the storage circuit. In this case, the processor reads the programs incorporated in its circuit and executes them to realize the respective functions. The processors described in connection with the above embodiment are not limited to single-circuit processors. A plurality of independent processors may be combined and integrated as one processor having multiple functions. Furthermore, a plurality of structural elements of the above embodiment may be integrated as one processor having multiple functions.

While certain embodiments have been described, these embodiments have been presented by way of example only, and are not intended to limit the scope. Indeed, the novel embodiments described herein may be embodied in a variety of other forms; furthermore, various omissions, substitutions and changes in the form of the embodiments described herein may be made without departing from the spirit. The accompanying claims and their equivalents are intended to cover such forms or modifications as would fall within the scope and spirit.

The invention claimed is:

1. A medical image processing apparatus, comprising:
a memory which stores volume data that includes a representation of a plurality of blood vessels connected to at least one of other blood vessels, and stores a plurality of target portions that are assigned for at least one of the plurality of blood vessels; and
processing circuitry configured to
extract the blood vessels from the volume data;
set a plurality of treatment orders for treating each of the plurality of target portions with a treatment;
simulate hemodynamics in the blood vessels when each of the target portions is treated in a first treatment order in the plurality of treatment orders:
simulate hemodynamics in the blood vessels when each of the target portions is treated in a second treatment order, different from the first treatment order, in the plurality of treatment orders; and
display a result comparing the simulated hemodynamics.

2. The medical image processing apparatus of claim 1, wherein the processing circuitry is further configured to:
recommend at least one treatment order based on the result of comparing the simulated hemodynamics.

3. The medical image processing apparatus of claim 2, wherein the processing circuitry is further configured to:

calculate a risk index value for each treatment order, based on a fluid parameter obtained by fluid analysis; and
present the at least one recommended treatment order, based on the calculated risk index value.

4. The medical image processing apparatus of claim 3, wherein the processing circuitry is further configured to:
calculate a fluid parameter at each analysis target portion determined on the blood vessels; and
use stability of the calculated fluid parameter as the risk index value.

5. The medical image processing apparatus of claim 3, wherein the processing circuitry is further configured to:
calculate a fluid parameter at each analysis target portion determined on the blood vessels; and
use a difference between the calculated fluid parameter and a predetermined threshold as the risk index value.

6. The medical image processing apparatus of claim 3, wherein the processing circuitry is further configured to:
generate a three-dimensional blood vessel model image from the volume data; and
display the calculated fluid parameter by color mapping on the blood vessels shown in the three-dimensional model image.

7. The medical image processing apparatus of claim 2, wherein the treatment is embolization in which an embolic agent s injected to embolize the blood vessels: and
the processing circuitry is further configured to simulate a behavior of the injected embolic agent by fluid analysis.

8. The medical image processing apparatus of claim 7, wherein the processing circuitry is further configured to:
perform the fluid analysis, using a kind of embolic agent, and an injection amount of the embolic agent, an injection position of the embolic agent as analysis parameters.

9. The medical image processing apparatus of claim 1, wherein the treatment is embolization by which to embolize the blood vessels.

10. A medical image diagnosis apparatus, comprising:
an imaging unit which captures a plurality of target portions of a subject and obtains image data;
a memory which stores the captured image data; and
processing circuitry configured to:
generate, from the image data, volume data that includes a representation of a plurality of blood vessels connected to at least one of other blood vessels, and store a plurality of target portions that are assigned for at least one of the plurality of blood vessels;
extract the blood vessels from the volume data;
set a plurality of treatment orders for treating each of the plurality of target portions with a treatment;
simulate hemodynamics in the blood vessels when each of the target portions is treated in a first treatment order in the plurality of treatment orders:
simulate hemodynamics in the blood vessels when each of the target portions is treated in a second treatment order, different from the first treatment order, in the plurality of treatment orders; and
display a result of comparing the simulated hemodynamics.

11. The medical image diagnosis apparatus of claim 10, wherein the processing circuitry is further configured to:
recommend at least one treatment order based on the result of comparing the simulated hemodynamics.

12. The medical image diagnosis apparatus of claim 11, wherein the processing circuitry is further configured to:
calculate a risk index value for each treatment order, based on a fluid parameter obtained by fluid analysis; and
present the at least one recommended treatment order, based on the calculated risk index value.

13. The medical image diagnosis apparatus of claim 12, wherein the processing circuitry is further configured to:
calculate a fluid parameter at each analysis target portion determined on the blood vessels; and
use stability of the calculated fluid parameter as the risk index value.

14. The medical image diagnosis apparatus of claim 12, wherein the processing circuitry is further configured to:
calculate a fluid parameter at each analysis target portion determined on the blood vessels; and
use a difference between the calculated fluid parameter and a predetermined threshold as the risk index value.

15. The medical image diagnosis apparatus of claim 12, wherein the processing circuitry is further configured to:
generate a three-dimensional blood vessel model image from the volume data; and
display the calculated fluid parameter by color mapping on the blood vessels shown in the three-dimensional model image.

16. The medical image diagnosis apparatus of claim 11, wherein the treatment is embolization in which an embolic agent is injected to embolize the blood vessels; and
the processing circuitry is further configured to simulate a behavior of the injected embolic agent by fluid analysis.

17. The medical image diagnosis apparatus of claim 16, wherein the processing circuitry is further configured to:
perform the fluid analysis, using a kind of embolic agent, and an injection amount of the embolic agent, an injection position of the embolic agent as analysis parameters.

18. The medical image diagnosis apparatus of claim 10, wherein the treatment is embolization by which to embolize the blood vessels.

19. A non-transitory computer-readable medium storing a computer-executable program which when executed by a computer, causes the computer to perform a method comprising:
acquiring volume data that includes a representation of a plurality of blood vessels connected to at least one of other blood vessels, and storing a plurality of target portions that are assigned for at least one of the plurality of blood vessels;
extracting the blood vessels from the volume data;
setting a plurality of treatment orders for treating each of the plurality of target portions;
simulating hemodynamics in the blood vessels when each of the target portions is treated in a first treatment order in the plurality of treatment orders:
simulating hemodynamics in the blood vessels when each of the target portions is treated in a second treatment order, different from the first treatment order, in the plurality of treatment orders; and
displaying a result of comparing the simulated hemodynamics.

20. A medical image processing apparatus, comprising:
a memory which stores volume data that includes a representation of a plurality of blood vessels connected to at least one of other blood vessels, and stores a plurality of target portions that are assigned for at least one of the plurality of blood vessels; and
processing circuitry configured to
extract the blood vessels from the volume data;
set a plurality of treatment orders for treating each of the plurality of target portions with a treatment;
simulate, for each target portion of the plurality of target portions, how hemodynamics in the vessel network changes when the target portions are treated in each of the plurality of set treatment orders;
display a result of comparing the simulated changes;
calculate a fluid parameter at each analysis target portion determined on the blood vessels;
use stability of the calculated fluid parameter or a difference between the calculated fluid parameter and a predetermined threshold as a risk index value for each treatment order; and
present at least one recommended treatment order, based on the calculated risk index value.

* * * * *